United States Patent [19]
DeSantis, Jr. et al.

[11] Patent Number: 5,705,510
[45] Date of Patent: Jan. 6, 1998

[54] USE OF CABERGOLINE AND RELATED ERGOLINE DERIVATIVES FOR CONTROLLING INTRAOCULAR PRESSURE

[75] Inventors: Louis DeSantis, Jr., Fort Worth; Verney L. Sallee, Burleson; Marsha A. McLaughlin, Joshua; Manoj L. Maniar, Fort Worth, all of Tex.

[73] Assignee: Alcon Laboratories, Inc., Fort Worth, Tex.

[21] Appl. No.: 547,755

[22] Filed: Oct. 25, 1995

Related U.S. Application Data

[63] Continuation of Ser. No. 108,859, Aug. 18, 1993, abandoned.

[51] Int. Cl.$^6$ ................................................ A61K 31/445
[52] U.S. Cl. ........................................ 514/323; 514/913
[58] Field of Search ................................. 514/323, 913

[56] References Cited

U.S. PATENT DOCUMENTS

| | | | |
|---|---|---|---|
| 4,501,749 | 2/1985 | Clineschmidt | 514/326 |
| 4,526,892 | 7/1985 | Salvati et al. | 514/288 |
| 4,722,933 | 2/1988 | Horn | 514/438 |
| 4,728,649 | 3/1988 | Mantegani et al. | 514/253 |
| 4,774,243 | 9/1988 | Baldwin | 514/229.5 |
| 4,847,253 | 7/1989 | Buonamici et al. | 514/253 |
| 4,861,793 | 8/1989 | Bernardi et al. | 514/410 |
| 5,110,606 | 5/1992 | Geyer | 424/489 |
| 5,151,272 | 9/1992 | Engstrom et al. | 424/450 |

FOREIGN PATENT DOCUMENTS

| | | | |
|---|---|---|---|
| 0 254 989 | 2/1988 | European Pat. Off. | C07C 91/28 |
| 0 317 269 A2 | 5/1989 | European Pat. Off. | A61K 31/48 |
| 0 091 313 | 9/1990 | European Pat. Off. | A61K 9/06 |
| 2 103 603 | 2/1983 | United Kingdom | C07D 457/04 |

OTHER PUBLICATIONS

Elibol, O., et al., *Intl. Ophthalmology*, "The effects of dopamine, haloperidol and bromocriptine on intraocular pressure", vol. 16, pp. 343–347 (1992).

Green, et al., *Exp. Eye Res.*, "Dopamine Stimulation of Passive Permeability and Secretion in the Isolated Rabbit Ciliary Epithelium", vol. 29, pp. 423–427 (1979).

Macri, et al., *Exp. Eye Res.*, "The Inhibitory Actions of Dopamine, Hydroxyamphetamine and Phenylephrine on Aqueous Humor Formation", vol. 26, pp. 85–89 (1978).

Mekki, et al., *The Lancet*, "Bromocriptine Lowers Intraocular Pressure Without Affecting Blood Pressure", pp. 1250–1251 (1983).

Potter, et al., *Curr Eye Res.*, "Effects of ergoline derivatives on intraocular pressure and iris function in rabbits and monkeys", vol. 2, pp. 281–288 (1983).

Potter, et al., *Curr. Eye Res.*, "Alteration in ocular function induced by phenylethylamine analogs of dopamine", vol. 3, pp. 851–859 (1984).

Shanon, et al., *Investigative Ophthalmology*, "The effect of dopamine on the intraocular pressure and pupil of the rabbit eye", vol. 15, pp. 371–380 (1976).

Hutton, J. T., et al., *Neurology*, "Controlled study of the antiparkinsonian activity and tolerability of cabergoline", vol. 43, pp. 613–616 (1993).

Karnezis, T. A., et al., *Trends In Pharmacological Science*, "Dopamine receptors and intraocular pressure", vol. 9, No. 11, pp. 389–390 (1988).

Potter, D. E., et al., *Current Eye Research*, "Ocular hypotensive action of ergoline derivatives in rabbits: effects of sympathectomy and domperidone pretreatment", vol. 3, No. 2, pp. 307–314 (1984).

Siegal, M. J., et al., *Experimental Eye Research*, "Effect of Topical Pergolide on Aqueous Dynamics in Normal and Glaucomatous Monkeys", vol. 44, No. 2, pp. 227–233 (1987).

Potter, D. E., et al. *Journal Of Ocular Pharmacology*, "LY141865: A Relatively Selective $DA_2$ Agonist with Complex Ocular Activity", vol. 4, No. 1, pp. 19–28 (1988).

Potter, D. E., et al., *Journal of Ocular Pharmacology*, "Cianergoline Lowers Intraocular Pressure in Rabbits and Monkeys and Inhibits Contraction of the Cat Nictitans by Suppressing Sympathetic Neuronal Function", vol. 3, No. 4, pp. 309–321 (1987).

Al–Sereiti, et al., *Proceedings of the BPS*, "The effects of a single oral dose of lisuride, terguride and bromocriptine on intraocular pressure", vol. 9, No. 11, p. 122P (Sep. 1987).

Geyer, et al., *Journal of Ocular Pharmacology*, "Hypotensive Effect of Bromocriptine in Normal Eyes", vol. 3, No. 1, pp. 1–4 (1987).

Geyer, et al., *Journal of Ocular Pharmacology*, "Hypotensive Effect of Bromocriptine in Glaucomatous Eyes", vol. 3, No. 4, pp. 291–294 (1987).

Al–Sereiti, et al., *Br. J. clin. Pharmac.*, "A comparison of the ocular hypotensive effect of 0.025% bromocriptine and 0.25% timolol eye drops in normal human volunteers", vol. 28, pp. 443–447 (1989).

Mekki, et al., *British Journal of Ophthalmology*, "Stimulation of dopamine receptors (type 2) lowers human intraocular pressure", vol. 69, pp. 909–910 (1985).

Al–Sereiti, et al., *Br. J. clin. Pharmac.*, "The effect of a single oral dose of pergolide on intraocular pressure and pupil diameter", vol. 28, pp. 263–268 (1989).

Al–Sereiti, et al., *Br. J. clin. Pharmac.*, "The effects of lisuride, terguride and bromocriptine on intraocular pressure (IOP)", vol. 27, pp. 159–163 (1989).

Primary Examiner—Zohreh Fay
Attorney, Agent, or Firm—Gregg C. Brown; Michael C. Mayo

[57] ABSTRACT

The use of certain dopaminergic compounds for controlling elevations of intraocular pressure is disclosed. The compounds are ergoline derivatives. The most preferred compound is cabergoline. The compounds have been found to produce a significant reduction of intraocular pressure.

9 Claims, No Drawings

USE OF CABERGOLINE AND RELATED ERGOLINE DERIVATIVES FOR CONTROLLING INTRAOCULAR PRESSURE

This is a continuation of application Ser. No. 08/108,859, filed Aug. 18, 1993, abandoned.

BACKGROUND OF INVENTION

The present invention relates to the treatment of glaucoma by controlling the principal symptom of that disease, elevated intraocular pressure. More specifically, the invention relates to the use of certain dopaminergic compounds to control intraocular pressure ("IOP") and thereby prevent or at least forestall progressive field of vision loss and other manifestations of glaucoma.

Glaucoma is a progressive disease which leads to optic nerve damage (i.e., glaucomatous optic neuropathy), and ultimately, partial or total loss of vision. The loss of visual field is secondary to the degeneration of optic nerve fibers which comprise the optic nerve. The causes of this disease have been the subject of extensive studies for many years, but are still not fully understood. However, it is known that a major risk factor for glaucomatous optic neuropathy is abnormally high IOP caused by an excess of intraocular fluid (i.e., aqueous humor) within the eye.

The usual reason for elevated IOP is an impairment of the outflow of aqueous humor from the eye. Although hypersecretion of aqueous humor is not considered to be a common factor for elevated IOP, the pressure may be reduced by inhibiting the production (i.e., inflow, secretion or formation) of aqueous humor by the ciliary processes of the eye. Beta adrenoceptor blockers and carbonic anhydrase inhibitors are examples of drug classes that lower intraocular pressure by inhibiting the inflow of aqueous humor. Other classes of drugs reduce IOP by increasing the outflow of aqueous humor from the eye. Examples of these drug classes include miotics, such as pilocarpine and carbachol, and adrenergics or sympathomimetics, such as epinephrine.

While the use of the drug classes stated above is common practice in the medical therapy of glaucoma, it is not without side effects. Each class suffers from causing a particular set of side effects, locally and/or systemically, that is related to the pharmacological actions of that class. For example, beta blockers, by blocking beta adrenoceptors in the heart can cause bradycardia or slow heart rate, and by blocking beta adrenoceptors in the bronchi can cause bronchoconstriction. Miotics can cause changes in visual accommodation to create blurred vision and brow ache. Systemic carbonic anhydrase inhibitors can cause malaise, headache, and other subjective symptoms which discourage their use by the patient. Since glaucoma medication must be taken over the patient's lifetime, it is beneficial to minimize side effects to encourage compliance with the prescribed therapy.

The present invention is directed to the use of a class of compounds which may be referred to as ergoline derivatives to control IOP. These compounds are believed to control IOP via an action on dopaminergic receptors.

The use of compounds having dopaminergic activity to control intraocular pressure is known. For example, U.S. Pat. No. 4,774,243 (Baldwin) describes the use of certain dopamine agonists to control elevated IOP.

SUMMARY OF THE INVENTION

The present invention is directed to the use of ergoline derivatives to control intraocular pressure. The compounds utilized in the present invention effectively control elevated intraocular pressure without causing many of the side effects associated with existing classes of therapeutic agents utilized in the treatment of glaucoma. For example, the compounds of the present invention do not act on the iris or the ciliary muscles of the eye, and therefore do not adversely affect visual acuity in the manner seen with the prior art use of miotics. The compounds of the present invention also represent an improvement over certain betablockers utilized in the prior art, particularly timolol, because the present compounds do not cause bronchoconstriction in pulmonary patients. Finally the compounds of the present invention have a relatively long duration of action compared to certain other agents used previously to treat glaucoma, and have a lower propensity to cause central nervous system-related side effects at doses which produce a useful reduction of intraocular pressure.

DESCRIPTION OF PREFERRED EMBODIMENTS

The ergoline derivatives of the present invention have the following general formula:

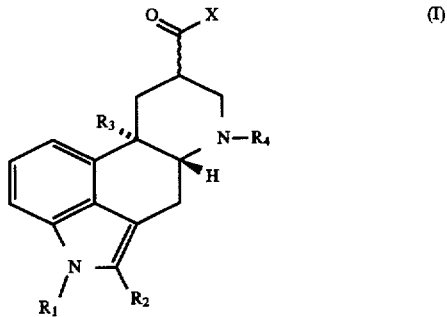

wherein:

$R_1$ represents a hydrogen atom or a methyl group;

$R_2$ represents a hydrogen or halogen atom, a methyl or formyl group or a group of the formula S—$R_7$ or SO—$R_7$, wherein $R_7$ represents an alkyl group having from 1 to 4 carbon atoms or a phenyl group;

$R_3$ represents a hydrogen atom or a methoxy group;

$R_4$ represents a hydrocarbon group having from 1 to 4 carbon atoms, benzyl or phenethyl; and X is OH or $NR_5CONHR_6$, wherein each of $R_5$ and $R_6$ independently represents an alkyl group having from 1 to 4 carbon atoms, a cyclohexyl group or a substituted or unsubstituted phenyl group or an acid and water-soluble group such as $(CH_2)_nN(CH3)_2$ in which n is an integer, with the proviso that $R_5$ and $R_6$ cannot both be a said acid and water soluble group;

and the pharmaceutically acceptable organic or inorganic acid salts and esters thereof. The possible halogen substituents are chlorine, bromine and fluorine; chlorine and bromine are preferred. In the definition of $R_5$ and $R_6$, n is preferably 1, 2, 3 or 4. In the definition of $R_4$, a hydrocarbon group having from 1 to 4 carbon atoms is intended to include alkyl, cycloalkyl and unsaturated (both ethylenically and acetylenically) groups. Representative moieties include methyl, ethyl, n-propyl, isopropyl, butyl, t-butyl, isobutyl, cyclopropyl, methylcyclopropyl, vinyl, allyl, and propargyl.

The wavy line (~) in formula (I) indicates that the substitutent in the 8-position may be either in the α-configuration, i.e., below the plane of the ring, or in the β-configuration, i.e., above the plane of the ring, or in both, i.e., a mixture thereof such as a racemic mixture. Preferably the substituent in the 8-position is in the β-configuration.

The compounds of formula (I) are known. See, for example, U.S. Pat. No. 4,526,892 (Salvati, et el), the entire contents of which are hereby incorporated in the present specification by reference. The compounds maybe synthesized in accordance with the teachings of the above-cited patent. The most preferred compound is cabergoline, which has the following structure:

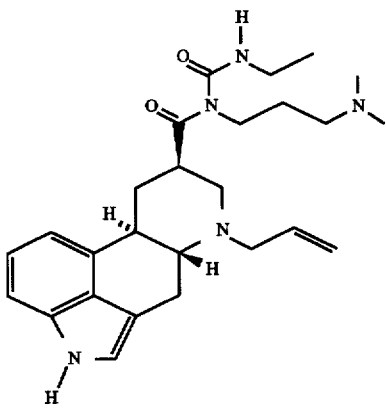

Cabergoline may also be identified as 1-[(6-allylergolin-8β-yl)carbonyl]-1-[3-(dimethyl-amino)propyl]-3-ethylurea.

One or more of the compounds, when contained in a suitable ophthalmic vehicle, are applied topically to the affected eye(s) to control intraocular pressure. A determination of the most appropriate type of composition for particular compounds will require consideration of various factors, including the partition coefficient, aqueous solubility, and degradation kinetics of the compounds. For example, cabergoline is hydrolytically unstable. It exhibits a significant degree of degradation in an aqueous environment at a neutral pH (i.e., it's $T_{90}$ at pH 7.0 and room temperature is less than 24 hours). It is relatively more soluble and stable at a pH in the range of 3 to 5 (i.e., it has been found to be relatively stable at a pH of 3 for up to 16 days), but compositions having an acidic pH may cause stinging when applied to the eye and therefore are not preferred.

In view of the relative instability of cabergoline, it is not possible to include this compound in aqueous solutions and other types of aqueous compositions which may be stored for relatively long periods (i.e., several months or more) prior to use. It is believed that other compounds of formula (I) may exhibit a similar instability. Although these compounds are soluble in medium chain triglycerides, such as miglyol, formulations based on the use of an oil as the vehicle for the active drug are not ideal. Among other things, the oil may obscure the vision of the patient, thereby adversely affecting patient compliance, and the high oil/water partition coefficient of the compounds may inhibit the bioavailability of the drug.

The present inventors have found that ophthalmic compositions known as "micro emulsions" are particularly well-suited for delivering cabergoline and other compounds of formula (I) to the eye via topical application. The preferred microemulsion compositions of the present invention include a non-aqueous internal phase and an external phase. The internal phase is a polar, pharmaceutically acceptable, oxygen-containing liquid such as $C_2$–$C_{30}$, preferably $C_2$–$C_{20}$-polyhydric alcohols, poly(ethylene or propylene) glycols with 4–200 repeating units, and the $C_1$–$C_5$ ether or $C_2$–$C_{30}$, preferably $C_2$–$C_{20}$ ester derivatives of any of the foregoing. Examples of such materials include: glycerin; propylene glycol; polyethylene glycol 200, 400, 600, 1500, 4000 and 6000; ethylene glycol dimethyl ether; and tetraethylene glycol dimethyl ether.

The preferred polar solvents for the internal phase include propylene glycol ("PG"), glycerol, ethylene glycol and polyethylene glycol. Some of these solvents, such as PG, also act as penetration enhancers. Thus, the use of such solvents in the compositions of the present invention also serves to improve the penetration of drug into the eye and thereby enhance the bioavailability of the drug. The microemulsions will contain the internal phase in an amount of from about 1 to about 30 percent by weight, based on the total weight of the composition ("wt. %"), preferably from about 5 to about 20 wt. %.

The external phase of the microemulsion may include a lower alkyl ester of a $C_{8-22}$ fatty acid, such as ethyl palmitate, isopropyl myristate ("IPM"), or medium chain triglycerides such as miglyols. IPM is preferred over the other esters such as ethyl laurate and ethyl caproate because of their characteristic odors. However, IPM has a slight stinging action when administered topically. Thus, super refined vegetable oils, such as peanut and corn oil, are preferred as the external phase. These oils are crystal clear and are more resistant to heat degradation than conventional oils. The microemulsions will contain the external phase in an amount of from about 31 to about 70 wt. %, preferably from about 40 to about 60 wt. %.

The microemulsions will contain an emulsifying agent in an amount of from about 10 to about 60 wt. %, preferably from about 10 to about 40 wt. %. The preferred emulsifier is lecithin; either egg or soy lecithin can be utilized. However, various other types of surfactants can also be utilized as the emulsifying agent.

The microemulsion preferably also includes a monoglyceride, such as mono myristoyl glycerol, glycerol mono oleate or glycerol mono linoleate, in an amount of from about 0.1 to about 5 wt. %, preferably from about 2 to about 5 wt. %. The advantage of adding a limited amount of monoglyceride in the formulation (i.e., up to about 5 wt. %) is that the formulation undergoes a phase change, which is very viscous, upon dilution with an aqueous fluid, such as tears. The increased viscosity serves to enhance the retention of the composition in the eye, and thereby enhances the bioavailability of the drug. When more than 5 wt. % of the monoglyceride is added to the composition, the viscosity of the microemulsion increases very quickly and the composition forms a semi-solid mass which is not easily droppable from a conventional dropper.

The preferred method of preparing the microemulsions of the present invention is to first dissolve the emulsifying agent in the external phrase, and then add one or more compounds of formula (I) to the internal phase. The internal and external phases are then combined and gently mixed to form a clear microemulsion.

The use of microemulsions such as those described above for oral administration of drugs is described in U.S. Pat. No. 5,110,606 (Geyer, et al.). The Geyer, et al. '606 patent maybe referred to for further details concerning the composition and preparation of such microemulsions. The entire contents of the Geyer, et al., '606 patent relating to the above-described microemulsions are hereby incorporated in the present specification by reference. The use of such microemulsions for purposes of topical ophthalmic administration of drugs is not disclosed in the Geyer, et al., '606 patent.

The non-aqueous microemulsions which may be utilized in the present invention are further illustrated by the following examples.

EXAMPLE 1

1 gm of egg lecithin was dissolved in 8 gms of isopropyl myristate by sonication. A 1% w/w solution (1 gm) of cabergoline in propylene glycol, with constant stirring, was added to the isopropyl myristate solution to obtain a clear microemulsion. The stability of cabergoline in this formulation was found to be improved by a factor of 70, as compared to the stability of cabergoline in an aqueous solution buffered at pH 7.0.

EXAMPLE 2

1 gm of egg lecithin was dissolved in 8 gms of isopropyl myristate by sonication. 500 mg of monomyristoyl glycerol (MMG) was then added and the resulting mixture was heated at 50° C. for five minutes. The heated mixture was then brought to room temperature and 1 gm of a 1% w/w solution of cabergoline in propylene glycol was added with constant stirring to obtain a clear microemulsion. This formulation undergoes an instantaneous phase change and becomes very viscous when diluted with water. The change in viscosity seen with addition of various amounts of water was measured using a Brookfield viscometer, Model LV and spindle CP52, at 100 rpm. The results are listed in the following table:

| Amount of Formulation (gms) | Amount of Water added (gms) | Viscosity (cps) Formulation – MMG | Formulation + MMG[a] |
|---|---|---|---|
| 1 | 0 | 9.9 | 9.9 |
| 1 | 0.1 | 9.4 | 14.9 |
| 1 | 0.3 | 17.9 | 10319 |
| 1 | 0.5 | 46.4 | 6741[b] |
| 1 | 0.7 | 58.8 | 5912[b] |

[a]measured at 0.6 rpm
[b]phase separation occurred

EXAMPLE 3

Brij 96 and monoolein are both solids. When they are mixed in the ratio of 10:90 they form a eutectic mixture. This solution forms a gel when it comes in contact with water. Thus, a 0.2% solution of cabergoline in the above mixture will not only stabilize the drug, but will also provide a sustained release of the drug upon application to the eye.

The compositions of the present invention may also be provided in lyophilized form (i.e., freeze-dried). The lyophilized drug is then reconstituted by means of dissolution in an aqueous vehicle just prior to use. Once the drug is placed in solution, it will be subject to the same degradation problems mentioned above. The composition can therefore only be utilized for a relatively short time following reconstitution. The length of time during which the composition can still be utilized will depend on the relative stability of the compound selected and the pH of the composition. However, such compositions will generally only remain viable for one to two weeks. This type of reconstituted compsition is further illustrated in the following example, which shows the formulation of a composition formed by combining a first part containing the cabergoline and at least a portion of the mannitol, in lyophilized form, and a second part containing the remaining ingredients in the form of an aqueous solution:

| Ingredient | Amount (wt. %) |
|---|---|
| Cabergoline | 0.25 |
| Citric acid, monohydrate | 0.1 |
| Mannitol | 4.5 |
| Disodium EDTA | 0.01 |
| Benzalkonium chloride | 0.01 |
| Sodium hydroxide and/or Hydrochloric acid | q.s. to adjust pH to 3.0 |
| Water | q.s. 100 |

The compositions of the present invention may also be formulated as aqueous solutions having a physiological pH, provided that the composition will be used within a short time (i.e., preferably 24 hours or less) following preparation. Thereafter, the therapeutic benefits of the compositions maybe lost or at least diminished due to degradation of the compounds of formula (I) contained therein. This type of extemporaneous composition is further illustrated in the following example:

| Ingredient | Amount (wt. %) |
|---|---|
| Cabergoline | 0.25 |
| Benzalkonium chloride | 0.01 |
| Edetate sodium | 0.05 |
| Sodium chloride | (to render isosmotic) |
| Hydrochloric acid and/or Sodium hydroxide | (to adjust pH) |
| Purified water | q.s. to 100% of volume |

In addition to one or more compounds of formula (I), the ophthalmic compositions of the present invention may also include various other ingredients, such as buffers, preservatives, co-solvents and viscosity building agents.

An appropriate buffer system (e.g., sodium phosphate or sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level of from 0.001% to 1.0% by weight.

Some of the compounds of formula (I) may have limited solubility in water and therefore may require a surfactant or other appropriate co-solvent in the composition. Such co-solvents include: Polysorbate 20, 60 and 80; Pluronic F-68, F-84 and P-103; cyclodextrin; or other agents known to those skilled in the art. Such co-solvents are typically employed at a level of from 0.01% to 2% by weight.

Viscosity greater than that of simple aqueous solutions maybe desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The establishment of a specific dosage regimen for each individual patient is left to the discretion of clinicians. The amount of compound administered will generally be in the range of from about 0.3 to about 3,600 micrograms per dose, preferably from about 3 to about 1,200 micrograms per dose. In general, the compounds of formula (I) will be administered by topically applying one to two drops of a solution or comparable amount of a microemulsion, suspension, solid, or semi-solid dosage form to the affected eye(s) one to four times per day. The concentration of the compounds of formula (I) in such compositions will vary, depending on the type of composition utilized. For example, it may be possible to use a relatively lower concentration of the compounds when compositions which provide for sustained release of the compounds or compositions which include a penetration enhancer are utilized. The concentrations generally will be in the range of from about 0.001 to about 12 wt. %, preferably from about 0.01 to 4 wt. %.

The ability of the compounds of formula (I) to control intraocular pressure has been demonstrated by means of laboratory experiments using animal models. The potential for ocular irritation and central nervous system side effects has also been evaluated.

EXAMPLE 6

Intraocular pressure (IOP) was determined in eyes of cynomolgus monkeys which had previously been treated with argon laser trabeculoplasty to induce ocular hypertension. The action of the test compound on IOP is expressed as percent reduction from baseline IOP measured before drug treatment. Treatment was by topical ocular administration of two 25 microliter aliquots of the formulation described in Example 5; the concentration of drug in the formulation was modified as needed to provide the total dose per eye indicated in the following table:

effective amount of a topical ophthalmic composition comprising an amount of a compound of the following formula effective to control intraocular pressure:

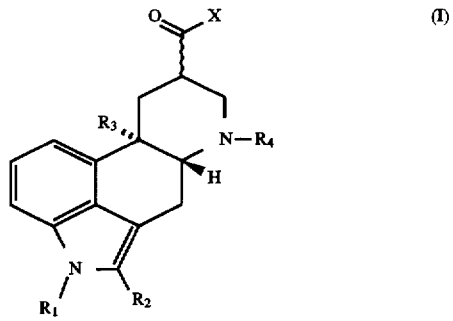

wherein:

$R_1$ represents a hydrogen atom or a methyl group;

$R_2$ represents a hydrogen or halogen atom, a methyl or formyl group or a group of the formula S—$R_7$ or SO—$R_7$, wherein $R_7$ represents an alkyl group having from 1 to 4 carbon atoms or a phenyl group;

$R_3$ represents a hydrogen atom or a methoxy group;

$R_4$ represents a hydrocarbon group having from 1 to 4 carbon atoms, benzyl or phenethyl; and X is OH or $NR_5CONHR_6$, wherein each of $R_5$ and $R_6$ independently represents an alkyl group having from 1 to 4 carbon atoms, a cyclohexyl group or a substituted or unsubstituted phenyl group or an acid and water-soluble group such as $(CH2)_nN(CH3)_2$ in which n is an integer, with the proviso that $R_5$ and R6 cannot both be a said acid and water soluble group; and a pharmaceutically acceptable vehicle therefor.

2. A method according to claim 1, wherein X is $NR_5CONHR_6$.

|  |  |  | Hours After Treatment | | | |
| --- | --- | --- | --- | --- | --- | --- |
| Drug Tested | Dose | Baseline IOP | 1 | 3 | 7 | 24 |
| Cabergoline | 5 µg | 31.0 ± 1.9 | 5.0 ± 1.9 | 12.4 ± 3.0 | 11.9 ± 2.2 | nd |
| Control |  | 32.0 ± 1.6 | 5.4 ± 3.4 | 5.3 ± 3.2 | 4.9 ± 3.0 | nd |
| Cabergoline | 5 µg | 32.8 ± 3.3 | 9.0 ± 2.9 | 6.1 ± 2.4 | 7.9 ± 3.4 | nd |
| Cabergoline | 15 µg | 30.2 ± 2.2 | 7.6 ± 1.6 | 6.1 ± 2.4 | 11.1 ± 2.8 | 8.2 ± 4.0 |
| Cabergoline | 50 µg | 34.7 ± 3.0 | 16.0 ± 2.4 | 30.6 ± 3.6 | 28.8 ± 5.5 | 27.3 ± 4.8 |
| Cabergoline | 500 µg | 36.0 ± 3.3 | 18.9 ± 4.5 | 29.9 ± 4.9 | 30.4 ± 4.5 | nd |
| Control |  | 38.2 ± 3.1 | 3.3 ± 4.0 | 1.3 ± 4.5 | 5.4 ± 3.8 | nd |

The foregoing data demonstrate that treatment with either 0.1% (50 µg) or 1% (500 µg) cabergoline produced a significant reduction of IOP, but lower concentrations had no effect on IOP. No side effects were observed in these animals, even though the total dose represented 15 to 20 times the dose per kilogram body weight which was administered to humans in published studies relating to potential systemic uses of this compound.

Cabergoline was also tested for acute ocular irritation in rabbits following topical ocular administration of two drops every 30 minutes for a total of ten doses of the formulation of Example 6. Ocular irritation results were unremarkable, with only a moderate iritis observed with this exaggerated dosing regimen.

What is claimed is:

1. A method of controlling elevations of intraocular pressure which comprises applying to the eye a therapeutically 3. A method according to claim 2, wherein the compound comprises cabergoline.

4. A method according to claim 1, wherein the pharmaceutically acceptable vehicle comprises a non-aqueous microemulsion.

5. A method according to claim 4, wherein the microemulsion comprises an internal phase, an external phase, and an emulsifying agent, said internal phase comprising a non-aqueous, oxygen-containing, pharmaceutically acceptable polar solvent, and said external phase comprising a lower alkyl ester of a $C_{8-22}$ fatty acid, a medium chain triglyceride or a super-refined vegetable oil.

6. A method according to claim 3, wherein the microemulsion further comprises a monoglyceride in an amount sufficient to enhance the viscosity of the microemulsion when it is topically applied to the eye.

7. A method according to claim 6, wherein the monoglyceride comprises mono myristoyl glycerol.

8. A method according to claim 5, wherein the polar solvent is selected from propylene glycol, glycerol, ethylene glycol and polyethylene glycol, and the external phase comprises a super-refined vegetable oil selected from peanut oil and corn oil.

9. A method according to claim 1, wherein the composition comprises a first part and a second part, the first part comprising said compound in the form of a lyophilized powder, and the second part comprising said pharmaceutically acceptable vehicle in the form of an aqueous, buffered solution.

* * * * *